(12) United States Patent
Vyavahare et al.

(10) Patent No.: US 12,570,954 B2
(45) Date of Patent: Mar. 10, 2026

(54) SYSTEMS AND METHODS FOR PROCESSING TISSUE

(71) Applicant: TGen Tech, LLC, Alpharetta, GA (US)

(72) Inventors: Narendra R. Vyavahare, Simpsonville, SC (US); Teodor Dan Simionescu, Pendleton, SC (US); Agnes Nagy-Mehesz, Simpsonville, SC (US); Ajay Houde, Alpharetta, GA (US)

(73) Assignee: Annoviant, Inc., Alpharetta, GA (US)

( * ) Notice: Subject to any disclaimer, the term of this patent is extended or adjusted under 35 U.S.C. 154(b) by 916 days.

(21) Appl. No.: 17/446,953

(22) Filed: Sep. 3, 2021

(65) Prior Publication Data

US 2022/0073869 A1 Mar. 10, 2022

Related U.S. Application Data

(60) Provisional application No. 63/075,048, filed on Sep. 4, 2020.

(51) Int. Cl.
*C12N 5/00* (2006.01)
*A61L 27/36* (2006.01)
*F16M 11/00* (2006.01)

(52) U.S. Cl.
CPC ........ *C12N 5/0081* (2013.01); *A61L 27/3633* (2013.01); *A61L 27/3691* (2013.01);
(Continued)

(58) Field of Classification Search
CPC ............. C12N 5/0081; C12N 2509/10; C12N 2533/90; A61L 27/3633; A61L 27/3691; A61L 2430/40; F16M 11/00
See application file for complete search history.

(56) References Cited

U.S. PATENT DOCUMENTS

| | | | |
|---|---|---|---|
| 3,740,779 A * | 6/1973 | Rubricuis ............ | A61B 5/1076 |
| | | | 606/1 |
| 6,107,081 A * | 8/2000 | Feeback .................. | G01N 3/08 |
| | | | 435/284.1 |
| 8,518,682 B2 | 8/2013 | Freyman | |

(Continued)

FOREIGN PATENT DOCUMENTS

| | | | |
|---|---|---|---|
| AU | 2011258295 B2 | 1/2015 | |
| CN | 205352856 U * | 6/2016 | |

(Continued)

OTHER PUBLICATIONS

Document entitled CN205352856U Realize Direct Tensile Test Device of Rock Sample, machine translation of CN 205352856 U provided by ProQuest, original document published 2016. (Year: 2016).*

(Continued)

*Primary Examiner* — Michael A Marcheschi
*Assistant Examiner* — Ashley Lopezlira
(74) *Attorney, Agent, or Firm* — Novel IP

(57) ABSTRACT

Embodiments of the present specification provide systems and methods for holding one or more tissues, such as veins, such that the tissue remains open in a chamber while undergoing orbital shaking with various solutions and to allow uniform treatment during a decellularization process. A frame is held on a stand to which the tissues are attached and comprises a tension inducing mechanism to cause the tissues to controllably stretch. The frame is removed from the stand, with the tissue attached to it, and placed in a decellularization chamber for uniform treatment of the tissue.

25 Claims, 7 Drawing Sheets

(52) U.S. Cl.
CPC ....... *A61L 2430/40* (2013.01); *C12N 2509/10* (2013.01); *C12N 2533/90* (2013.01); *F16M 11/00* (2013.01)

(56) References Cited

U.S. PATENT DOCUMENTS

| | | | |
|---|---|---|---|
| 8,623,066 B2 | 1/2014 | Looi | |
| 8,784,890 B2 | 7/2014 | Farrell | |
| 9,091,392 B1 * | 7/2015 | Addington | ............. F16M 11/10 |
| 9,987,120 B2 | 6/2018 | Soletti | |
| 10,076,427 B2 | 9/2018 | Soletti | |
| 10,085,829 B2 | 10/2018 | Soletti | |
| 10,149,750 B2 | 12/2018 | Wagner | |
| 10,695,162 B2 | 6/2020 | Soletti | |
| 10,876,222 B2 | 12/2020 | Edouard Naz et al. | |
| 2006/0228252 A1 * | 10/2006 | Mills | ..................... A61L 2/0088 |
| | | | 422/28 |
| 2012/0028234 A1 * | 2/2012 | Guertin | .................. C12M 23/28 |
| | | | 435/395 |
| 2012/0183944 A1 | 7/2012 | Taylor | |
| 2016/0022254 A1 * | 1/2016 | McCarthy | ............... A61L 27/50 |
| | | | 600/208 |
| 2017/0065744 A1 * | 3/2017 | Anderson-Cunanan | ..................... |
| | | | A61L 27/3625 |
| 2018/0368966 A1 | 12/2018 | Soletti | |
| 2019/0390152 A1 * | 12/2019 | Li | .......................... C12M 41/48 |

FOREIGN PATENT DOCUMENTS

| | | | | | |
|---|---|---|---|---|---|
| GB | 2450718 A | * | 1/2009 | ........... | C12M 35/04 |
| WO | 2009064806 A1 | | 5/2009 | | |
| WO | 2015181245 A1 | | 12/2015 | | |
| WO | WO-2018149795 A1 | * | 8/2018 | ........... | C12M 35/04 |
| WO | 2022101370 A1 | | 5/2022 | | |

OTHER PUBLICATIONS

International Search Report for PCT/US21/71375, Jan. 26, 2022.

* cited by examiner

SYSTEMS AND METHODS FOR PROCESSING TISSUE

CROSS-REFERENCE

The present application relies on U.S. Patent Provisional Application No. 63/075,048, titled "Systems and Methods for Processing Tissue" and filed on Sep. 4, 2020, for priority and is herein incorporated by reference in its entirety.

FIELD

The present specification relates to the systems and methods for processing tissue in order to decellularize the tissue. More particularly, the present specification relates to a structure for holding animal vasculature, such as bovine jugular veins, and processing the animal vasculature to achieve a predetermined amount of decellularization.

BACKGROUND

Extracellular matrix (ECM) is a complex molecular three-dimensional network of proteins and carbohydrates that is released by animal cells into the extracellular space. The network of ECM components provide an anchor surrounding cellular compartments in tissues and organs. The ECM molecules and their respective assemblies provide a structural and instructive scaffold during development and throughout life that endows tissues with tensile strength, elasticity, hydration, and the ability to withstand mechanical forces. The ECM also plays a vital role in maintaining cells homeostasis. The ECM molecules function as a repository for growth factors, cytokines, and proteinases. Each tissue has an ECM with a unique biochemical composition, structure that is generated during tissue development. ECM receptors, such as integrins, discoidin domain receptors and syndecans, mediate cell adhesion to the ECM. The cell adhesion further mediates cytoskeletal coupling to the ECM. The dynamic modelling of the ECM structure guide fundamental cellular processes including differentiation, proliferation, migration, and survival.

ECM is known to aid in regrowth and healing of tissue. In human fetuses, the ECM works with stem cells to grow and regrow all parts of the human body. ECM is also useful in repairing wounds and injuries, and for tissue engineering. The ECM prevents the immune system from triggering during an injury and responding with inflammation. The ECM also enables the cells surrounding the injury to repair the injured tissue and prevent forming of scar tissue. Medically, ECM can be extracted from animal tissues using a biochemical process. The extracted ECM is currently used for many applications such as treating ulcers by closing the hole in the tissue that lines the stomach, for treating wounds, as well as to support three-dimensional cell culture in vitro for modelling tumor development.

Decellularization refers to the process of treating a tissue to isolate the extracellular matrix (ECM) component of the tissue from its inhabiting cells. Some methods of decellularization involve immersing the tissue in fluids in a sealed chamber autoclaving at high temperatures, such as 121° C., which leaves an ECM scaffold of the original tissue. The ECM scaffold can be used for generating an artificial organ and for tissue regeneration.

The process of treatment of the tissue is critical and uniform treatment of the tissue is important for maintaining the structural and chemical integrity of the original tissue in the resulting ECM scaffold. Therefore, there is a need for systems and methods that enable decellularization at all levels, and evenly throughout the tissue.

SUMMARY

The following embodiments and aspects thereof are described and illustrated in conjunction with systems, tools and methods, which are meant to be exemplary and illustrative, and not limiting in scope. The present application discloses numerous embodiments.

In some embodiments, the present specification discloses a processing device adapted to decellularize one or more pieces of biological tissue, comprising: a frame configured to hold the one or more pieces of biological tissue; a first holder configured to atraumatically attach to a periphery of one open end of at least one of the one or more pieces of biological tissue; a second holder configured to atraumatically attach to a periphery of an opposing open end of the at least one of the one or more pieces of biological tissue; a first member configured to attach the first holder to the frame; and a second member configured to attach the second holder to the frame, wherein at least one of the first member or second member is configured to lengthen or contract so as to apply tension to the at least one of the one or more pieces of biological tissue.

Optionally, the one or more pieces of biological tissue comprises a vein.

Optionally, the one or more pieces of biological tissue number in a range of 4 to 10.

Optionally, the first holder is configured to atraumatically attach to the entire periphery of the one open end of the at least one of the one or more pieces of biological tissue.

Optionally, the second holder is configured to atraumatically attach to the entire periphery of the opposing open end of the at least one of the one or more pieces of biological tissue.

Optionally, the processing device further comprises a first measurement member attached to a first side of the frame, wherein the first measurement member comprises a plurality of measurement units.

Optionally, the first measurement member is vertically positioned and is configured as a cylinder with a tapering diameter across at least part of its length.

Optionally, the processing device further comprises a second measurement member attached to an opposing second side of the frame, wherein the second measurement member comprises a plurality of measurement units.

Optionally, the second measurement member is vertically positioned and is configured as a cylinder with a tapering diameter across at least part of its length.

Optionally, the frame comprises a top member extending along a top side of the frame and a bottom member extending along a bottom side of the frame.

Optionally, the top member comprises at least one first threaded hole, wherein the bottom member comprises at least one second threaded hole and wherein the at least one second threaded hole is vertically aligned with the at least one first threaded hole.

Optionally, the first holder comprises a first ring adapted to atraumatically grasp the periphery of the one open end of the at least one of the one or more pieces of biological tissue and a first semi-circular loop fixedly attached to opposite sides of the first ring, wherein the first semi-circular loop comprises a first protrusion at a center of the first semi-circular loop.

Optionally, the second holder comprises a second ring adapted to atraumatically grasp the periphery of the open opposing end of the at least one of the one or more pieces of biological tissue and a second semi-circular loop fixedly attached to opposite sides of the second ring, wherein the second semi-circular loop comprises a second protrusion at a center of the second semi-circular loop.

Optionally, the first member is at least one first threaded screw, wherein the at least one first threaded screw is configured to pass through the first protrusion and the at least one first threaded hole and wherein the at least one first threaded screw is further configured to apply said tension upon being turned.

Optionally, the second member is at least one second threaded screw, wherein the at least one second threaded screw is configured to pass through the second protrusion and the at least one second threaded hole and wherein the at least one second threaded screw is further configured to apply said tension upon being turned.

Optionally, the processing device further comprises a stand adapted to support the frame during mounting of a tissue, wherein the stand comprises a base surface configured to be horizontally positioned on a flat surface and a pair of vertically protruding hollow extensions perpendicularly and fixedly attached to the base surface and wherein each extension is configured to attach to one end of the first measurement member.

Optionally, the processing device further comprises a zip tie, wherein the zip tie is adapted to secure at least one of the first holder to the periphery of the one open end of the at least one of the one or more pieces of biological tissue or the second holder to the periphery of the opposing open end of the at least one of the one or more pieces of biological tissue.

Optionally, the first ring has a first diameter and the protrusion has a second diameter and wherein the first diameter is larger than the second diameter.

Optionally, the at least one of the first member or second member is configured to apply the tension to elongate the at least one of the one or more pieces of biological tissue in a range of 2 to 10 percent.

Optionally, the processing device further comprises a third holder configured to atraumatically attach to a periphery of one open end of at least a second one of the one or more pieces of biological tissue; a fourth holder configured to atraumatically attach to a periphery of an opposing open end of the at least second one of the one or more pieces of biological tissue; a third member configured to attach the third holder to the frame; and a fourth member configured to attach the fourth holder to the frame, wherein at least one of the third member or fourth member is configured to lengthen or contract so as to apply tension to the at least second one of the one or more pieces of biological tissue.

Optionally, the processing device further comprises a fifth holder configured to atraumatically attach to a periphery of one open end of at least a third one of the one or more pieces of biological tissue; a sixth holder configured to atraumatically attach to a periphery of an opposing open end of the at least third one of the one or more pieces of biological tissue; a fifth member configured to attach the fifth holder to the frame; and a sixth member configured to attach the sixth holder to the frame, wherein at least one of the fifth member or sixth member is configured to lengthen or contract so as to apply tension to the at least third one of the one or more pieces of biological tissue.

Optionally, the processing device further comprises a seventh holder configured to atraumatically attach to a periphery of one open end of at least a fourth one of the one or more pieces of biological tissue; an eighth holder configured to atraumatically attach to a periphery of an opposing open end of the at least fourth one of the one or more pieces of biological tissue; a seventh member configured to attach the seventh holder to the frame; and an eighth member configured to attach the eighth holder to the frame, wherein at least one of the seventh member or eighth member is configured to lengthen or contract so as to apply tension to the at least fourth one of the one or more pieces of biological tissue.

Optionally, the processing device further comprises a ninth holder configured to atraumatically attach to a periphery of one open end of at least a fifth one of the one or more pieces of biological tissue; a tenth holder configured to atraumatically attach to a periphery of an opposing open end of the at least fifth one of the one or more pieces of biological tissue; a ninth member configured to attach the ninth holder to the frame; and a tenth member configured to attach the tenth holder to the frame, wherein at least one of the ninth member or tenth member is configured to lengthen or contract so as to apply tension to the at least fifth one of the one or more pieces of biological tissue.

Optionally, the processing device further comprises an eleventh holder configured to atraumatically attach to a periphery of one open end of at least a sixth one of the one or more pieces of biological tissue; a twelfth holder configured to atraumatically attach to a periphery of an opposing open end of the at least sixth one of the one or more pieces of biological tissue; an eleventh member configured to attach the eleventh holder to the frame; and a twelfth member configured to attach the twelfth holder to the frame, wherein at least one of the eleventh member or twelfth member is configured to lengthen or contract so as to apply tension to the at least sixth one of the one or more pieces of biological tissue.

Optionally, each of the first holder and second holder, third holder and fourth holder, fifth holder and sixth holder, and seventh holder and eighth holder are vertically aligned with each other.

In some embodiments, the present specification discloses a tissue processing device, comprising: a frame configured to hold one or more tissues, the frame comprising: two parallel scales fixedly attached to two opposite sides of the frame, each scale comprising an elongated cylinder, an outer surface of the elongated cylinder marked with the scale; two parallel bars fixedly attached to the remaining two opposite sides of the frame, comprising: a top bar positioned on a top side of the frame, comprising at least one threaded hole attached on a side of the longitudinal axis of the top bar; and a bottom bar positioned on a bottom side of the frame and parallel to the top bar, comprising at least one threaded hole wherein each threaded hole is vertically aligned with a corresponding threaded hole on the top bar; at least two tissue fitting structures comprising a first ring for attaching a tissue and a semi-circular loop fixedly attached to diametrically opposite sides of the first ring, wherein the semi-circular loop comprises a protrusion at a center of the semi-circular loop, wherein a first of the at least two tissue fitting structures is configured to attach to the top bar and a second of the at least two tissue fitting structures is configured to attach to the bottom bar; at least one first threaded screw, configured to pass through the protrusion of the first of the at least two tissue fitting structures and the at least one threaded hole in the top bar configured to attach the first of the at least two tissue fitting structures; and at least one second threaded screw that is configured to pass through the protrusion of the second of the at least two tissue fitting structures and the at least one threaded hole in the bottom bar configured to attach to the second of the at least two tissue fitting structures to the frame.

Optionally, the tissue processing device further comprises a stand to support the frame during mounting of a tissue, the stand comprising: a base surface configured to be horizontally positioned on a flat surface; and a pair of vertically protruding hollow extensions perpendicularly and fixedly attached to the base surface, each extension configured to attach with one end of a scale.

Optionally, each scale comprises a top end and a bottom end and wherein each bottom end comprises a vertically protruding elongated cylinder configured to be removably positioned within the corresponding vertically protruding hollow extensions fixedly attached to the base surface.

Optionally, a first of the at least two tissue fitting structures is configured to attach a first opening of a cylindrical tissue and a second of the at least two tissue fitting structures is configured to attach a second opening of the cylindrical tissue.

Optionally, a zip tie is used to attach the first and the second openings of the tissue to the first rings of the first and the second of the at least two tissue fitting structures, respectively.

Optionally, the first and the second of the at least two tissue fitting structures are respectively attached with the frame with a threaded hole on the top bar and a threaded hole on the bottom bar that is vertically aligned with the threaded hole on the top bar.

Optionally, the first ring has a first diameter and the protrusion has a second diameter, and wherein the first diameter is larger than the second diameter.

Optionally, each scale is configured to measure an initial and a final length of a tissue that is mounted on the frame.

Optionally, the at least one threaded screw is configured to be adjusted to apply a tension to elongate a tissue attached to the at least two tissue fitting structures.

Optionally, the at least one threaded screw is configured to be adjusted to apply the tension to elongate the tissue in a range of 2 to 10 percent.

In some embodiments, the present specification discloses a tissue processing device, comprising: a rectangular frame configured to hold one or more veins, the frame comprising: two parallel scales fixedly attached to two opposite sides of the frame, each scale comprising an elongated cylinder, an outer surface of the elongated cylinder marked with the scale; two parallel bars fixedly attached to the remaining two opposite sides of the frame, comprising: a top bar positioned on a top side of the frame, comprising at least one threaded hole attached on a side of the longitudinal axis of the top bar; and a bottom bar positioned on a bottom side of the frame and parallel to the top bar, comprising at least one threaded hole wherein each threaded hole is vertically aligned with a corresponding threaded hole on the top bar; at least two tissue fitting structures comprising a first ring for attaching a tissue and a semi-circular loop fixedly attached to diametrically opposite sides of the first ring, wherein the semi-circular loop comprises a second ring at a center of the semi-circular loop, wherein one of the two tissue fitting structures is configured to attach to the top bar and the other of the two tissue fitting structures is configured to attach to the bottom bar; and at least one spring mechanism, configured to attach to a first tissue fitting structure of the at least two tissue fitting structures to the frame.

Optionally, the tissue processing device further comprises a stand to support the frame during mounting of a tissue, the stand comprising: a base surface configured to be horizontally positioned on a flat surface; and a pair of vertically protruding hollow extensions perpendicularly and fixedly attached to the base surface, each extension configured to attach with one end of a scale.

Optionally, each scale comprises a top end and a bottom end and wherein each bottom end comprises a vertically protruding elongated cylinder configured to be removably positioned within the corresponding vertically protruding hollow extensions fixedly attached to the base surface.

Optionally, a first of the at least two tissue fitting structures is configured to attach a first opening of a cylindrical tissue and a second of the at least two tissue fitting structures is configured to attach a second opening of the cylindrical tissue.

Optionally, a zip tie is used to attach the first and the second openings of the tissue to the first rings of the first and the second of the at least two tissue fitting structures, respectively.

Optionally, the first and the second of the at least two tissue fitting structures are respectively attached with the frame with a hole on the top bar and a hole on the bottom bar that is vertically aligned with the hole on the top bar.

Optionally, the first ring has a first diameter and the second ring has a second diameter, and wherein the first diameter is larger than the second diameter.

Optionally, each scale is configured to measure an initial and a final length of a tissue that is mounted on the frame.

Optionally, the at least one spring is configured to be adjusted to apply a tension to elongate a tissue attached to the at least two tissue fitting structures.

Optionally, the at least one spring is configured to be adjusted to apply the tension to elongate the tissue in a range of 2 to 10 percent.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

The present specification is directed toward providing systems and methods for holding one or more veins so that the veins remain open in a chamber while undergoing orbital shaking with various solutions to allow uniform treatment during a decellularization process. Components of the system in accordance with the embodiments are autoclavable at 121° C. Different types of tissues, including veins such as bovine jugular vein, arteries, vena cava, also any tissue-derived tubular scaffolds or synthetic polymers, may be treated by the embodiments of the present specification.

In embodiments, the systems and methods may include an automatic solution changing system comprising at least one chamber from which solution can be drawn. In embodiments, the automatic solution changing system may be programmable, wherein the programming capability may be integrated with the system or remote, wired or wirelessly, and optionally, using a controller.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used in this specification, the terms "vein" and "conduit" may be used interchangeably to refer to a structure comprised of tissue that defines a lumen such that it forms an open-tube or open cylindrical structure.

Frame of the Vein Preparation Device

Figure 1A:
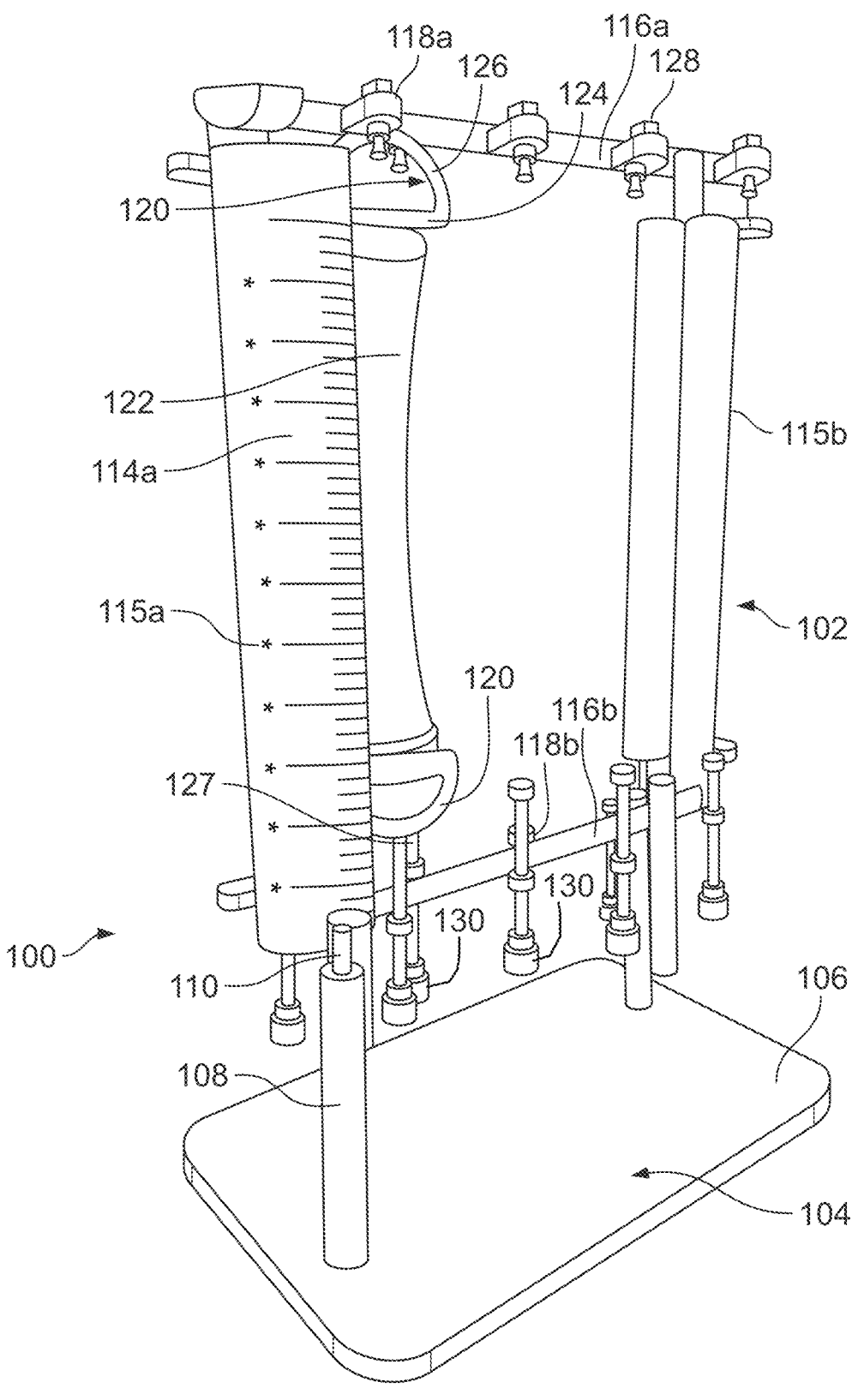
FIG. 1A illustrates an exemplary structure of a tissue processing device, in accordance with some embodiments of the present specification.

FIG. 1A illustrates an exemplary structure 100 of a tissue processing device, in accordance with some embodiments of the present specification. The structure 100 includes a frame 102 that is supported by a stand 104. The stand 104 comprises a base surface 106, which in some embodiments is a flat rectangular plate. The base surface 106 further supports at least two vertically protruding hollow extensions 108 that are perpendicularly and fixedly attached to the base surface 106. The two extensions 108 are positioned proximal to diagonally opposite corners of the rectangular base surface 106. The hollow extensions 108 are configured to receive and house elongated tubes 110 that extend from the frame 102, thus providing a mechanism to support the frame 102. The stand 104 is used to support the frame 102 during mounting of a tissue in the form of a vein or conduit 122. In embodiments, once the tissue is mounted on the frame 102, the frame 102 is removed from the stand 104 by withdrawing the tubes 110 from the hollow extensions 108 fixed on the stand 104. The frame 102 is subsequently placed within a chamber for processing the tissue.

It should be appreciated that the stand may have any configuration which provides for a stable surface capable of receiving a frame. The mechanism of attaching the frame to the stable surface may comprise a male/female connection mechanism in which a male (or female) structure on the frame is configured to receive or be inserted into, in a complementary manner, a corresponding female (or male) structure on the stand. The mechanism of attaching the frame to the stable surface may alternatively comprise a protrusion/slot mechanism in which a protrusion (or slot) structure on the frame is configured to receive or be inserted into, in a complementary manner, a corresponding slot (or protrusion) structure on the stand. The mechanism of attaching the frame to the stable surface may alternatively comprise a magnetic mechanism in which a ferromagnetic material (or magnet) structure on the frame is configured to be attracted to, and thereby attach to, in a complementary manner, a corresponding magnet (or ferromagnetic material) structure on the stand.

The frame 102 itself is configured as a geometric shape, such as a polygon or, more specifically, a rectangle. When the frame 102 is supported on the stand 104, the frame 102 is positioned vertically with two parallel vertical sides 115$a$, 115$b$ that are configured to be attached to the stand 104, as described above, and two parallel horizontal sides 116$a$, 116$b$ which are also its top and bottom sides. In embodiments, each of the two vertical sides include a scale 114$a$ with physical markings. The scale 114$a$ is structured in the form of an elongated member, such as a tube or cylinder, where the outer surface of the member comprises the physical markings. In embodiments, the physical markings indicate a measurement of length, in units such as inches, millimeters or centimeters. In embodiments, the physical markings on the scale may provide annotations of various physical lengths and/or varying units and are presented incrementally. Thus, in an embodiment, the scale 114$a$ may be used to measure a length of the vein or conduit 122.

Figure 1B:
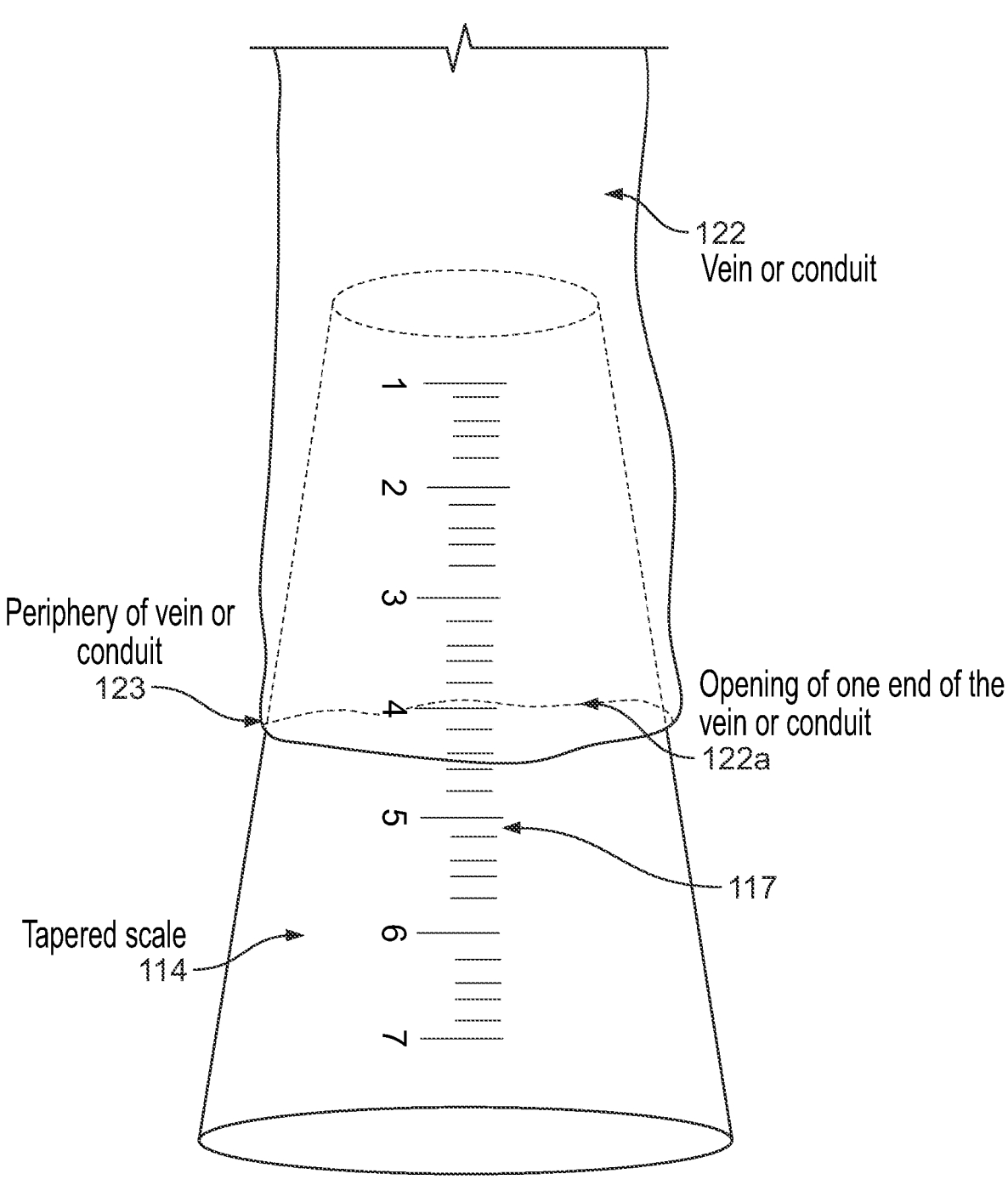
FIG. 1B illustrates an exemplary structure of a measuring device that may be used with the tissue processing device of FIG. 1A, to measure the diameter of a vein or conduit, in accordance with some embodiments of the present specification.

In some optional embodiments, the scale 114$a$ has a cylindrical shape with a constantly varying or partially varying diameter across its longitudinal length. In one embodiment a tapered scale 114 has a conical or tapered cylindrical shape. FIG. 1B illustrates an exemplary structure of a measuring device or tapered scale 114 that may be used with the tissue processing device of FIG. 1A, that may be used to measure a diameter of a vein or conduit 122, in accordance with some embodiments of the present specification. Operationally, a user may first position an opening 122$a$ of one end of the vein or conduit 122 over the portion of the tapered scale 114 having a smaller width or radius and then continue inserting the tapered scale 114 into, and through, the opening of one end of the vein or conduit 122 until the periphery 123 of the vein or conduit 122 snugly fits around the scale. The point where the periphery 123 of the vein or conduit 122 snugly contacts the scale may be considered the diameter of the vein or conduit 122. In optional embodiments, a length may also be measured using the tapered scale 114.

Referring back to FIG. 1A, in some embodiments, the two parallel horizontal sides are configured as two horizontal parallel bars-a top bar 116a and a bottom bar 116b. The bars 116a and 116b are fixedly attached to the remaining two opposite sides at the ends of the scale 114a. The top bar 116a is positioned on the top side of the frame 102. The bottom bar 116b is positioned on the bottom side of the frame 102 and is parallel to the top bar 116a. Both bars 116a and 116b include one or more first openings 118a and second openings 118b attached on their sides along their length. The numbers of first openings 118a and second openings 118b on the top and bottom bars 116a and 116b are equal and aligned to each other in pairs in a vertical direction. Each first opening 118a and second opening 118b is configured to receive a screw to attach one or more tissues. Each pair of first openings 118a and second openings 118b, which are vertically aligned can receive a corresponding set of screws that are configured to support attachment for a single piece of tissue.

Tissue Attachment and Tension System

In embodiments, tissue fitting structures 120 are used to attach a tissue such as the vein 122, to the frame 102. The vein 122 is attached using the two tissue fitting structures 120, one on each of the vein's opposing end.

Figures 4A, 4B:
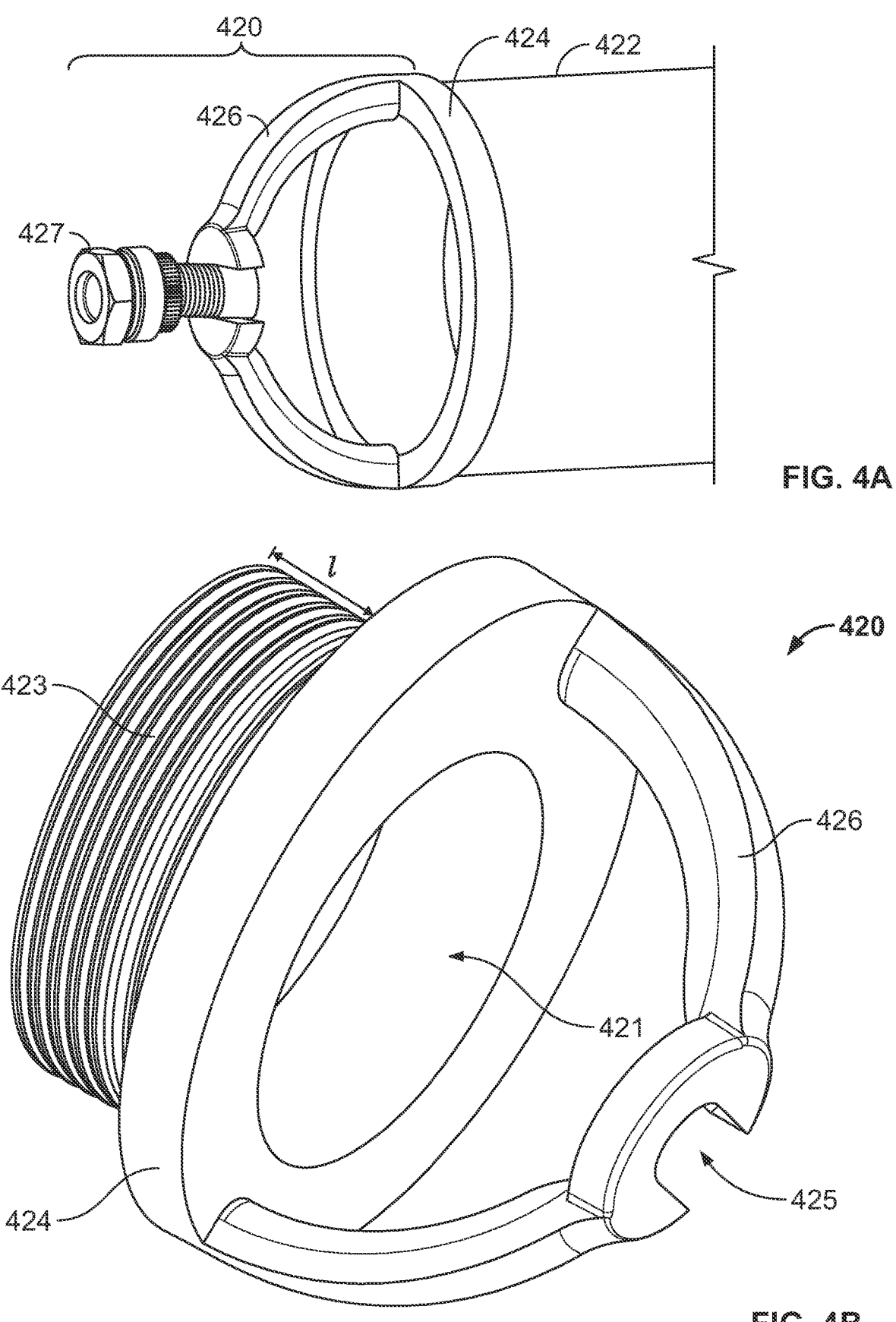
FIG. 4A illustrates a vein attached to a tissue fitting structure with a first ring, in accordance with some embodiments of the present specification.
FIG. 4B is an illustration of a tissue fitting structure in accordance with some embodiments of the present specification.

An exemplary tissue fitting structure 120 comprises a semi-circular loop 126 fixedly attached to a first ring portion 124. In some alternate embodiments, other shapes of loops 126 are used to attach to the first ring portion 124. The two ends of the semi-circular loop 126 are fixed to the diametrically opposite sides on the first ring portion 124. The semi-circular loop 126 further includes a connecting structure 127, which may be a protrusion, a second ring, hook, or any structure capable of being connected with a mating structure in the center of its circumference such that the connecting structure 127 (in this embodiment, a second ring) is parallel to the first ring portion 124. In embodiments, a diameter of the second ring 127 is less than a diameter of the first ring portion 124. Referring to FIGS. 4A and 4B, the tissue fitting structure 420 comprises a first ring 424 which may be circular or elliptical in shape. In one embodiment, the first ring 424 may have one or more inner diameters in a range from a first diameter of 11 mm to a second diameter of 29 mm. Attached to the first ring 424 is a connecting structure 426, which is preferably a semi-circular arc or loop 426. The semi-circular arc 426 has a first end and a second end which are fixedly attached to the first ring 424. At the top of the semi-circular arc 426, and preferably aligned with the center of the first ring 424, is a connecting structure 427, which may be a protrusion, a second ring, hook, or any structure capable of being connected with a mating structure. In some embodiments, connecting structure 427 comprises an adjustable screw for adjusting tension on the attached vein or conduit 422. The connecting structure 427 is configured to be positioned in an opening 425 at a first end of the tissue fitting structure 420 on the semi-circular arc 426. In embodiments, the tissue fitting structure 420 includes an annular member 423 on a second end opposite the first end, such that the tissue fitting structure 420 approximates a 'T' shaped cork structure with a lumen 421 inside or positioned therein. The annular member 423 is configured to receive an end of the vein or conduit 422 and secure the vein or conduit 422 to the tissue fitting structure 420. In some embodiments, the end of the vein or conduit 422 is secured to the annular member 423 using a length of suture, wire, cable, or zip tie. In some embodiments, a length/of the annular member 423 is at least 0.25 mm to allow a zip tie to be secured about the end of the vein or suture 422. In some embodiments, a diameter of the vein or conduit 422 may be measured using the annular member 423, as an outer diameter of the annular member 423 approximates an inner diameter of the vein or conduit 422. In some embodiments, referring to FIGS. 1B, 4A, and 4B simultaneously, the annular member is tapered and a diameter of the vein or conduit is measured by positioning the vein or conduit on the tapered scale 114 until a periphery of the vein or conduit 123 is fitted snugly on the tapered scale 114. A diameter of the vein or conduit may then be read from a scale 117 on the tapered scale.

Referring back to FIG. 1A, one end of the vein 122 is attached to a first ring portion 124 of the tissue fitting structure 120. The vein 122 is attached to the circumference of the first ring portion 124. In some embodiments, a zip-tie is used to fix one end of the vein 122 to the first ring portion 124. In alternate embodiments, other methods may be used to fix the vein 122 to the first ring portion 124, such as including but not limited to suturing or elastic bands. The vein 122 is fixed at its both ends similarly with tissue fitting structures 120. Once connected, the two ends of the vein 122 are connected to the two tissue fitting structures 120, and the two tissue fitting structures 120 are attached to the frame 102 using the connecting structure 127.

In one embodiment, the top bar 116a comprises a plurality of first openings 118a, horizontally spaced apart by a minimum distance of 25 mm such that two veins or conduits may be fitted side by side without touching one another. In some embodiments, the maximum inner diameter for the fitting rings is 19 mm. The bottom bar 116b comprises a complementary set of second openings 118b that align with the first openings 118a (such that a line drawn from a first opening to an aligned second opening would be normal to the base of the stand) which are also horizontally spaced apart by a minimum distance of 25 mm. A screw 128 is attached to the connecting structure 127 and threaded through first openings 118a on the top bar 116a to attach the tissue fitting structure, and therefore one end of the vein 122, to the top side of the frame 102. In embodiments, the screw 128 is a flat head screw. The screw 128 may be rotated through the first openings 118a on the top bar 116a for as far as it may move so as to fix the corresponding tissue fitting structure 120 to the top bar 116a of the frame 102.

In embodiments, the vein 122, after attaching to the top bar 116a, is attached to the bottom bar 116b with the same means and process as the attachment with the top bar 116a, except that an adjustable screw 130 is mated to a connecting structure 127 of the tissue fitting structure 120 and threaded through second openings 118b on the bottom bar 116b. The adjustable screw 130 is rotated through the second openings 118b in the bottom bar 116b until the vein 122 is extended to a desired length. Thus, the adjustable screw 130 is used to apply tension to the vein 122 to elongate the vein 122 between the two tissue fitting structures 120 on its either ends.

It should be appreciated that, while an adjustable screw is described as the means by which the tissue fitting structures are attached to the top or bottom bars, other mechanisms may be used, including any protrusion or member that can a) releasably attach to the connecting structure 127 of the tissue fitting structure 120 and b) connect to the top bar 116a or bottom bar 116b of the frame 102. A screw mechanism is preferred because it allows for the controlled extension or stretching of the vein, as further described below.

Figure 2:
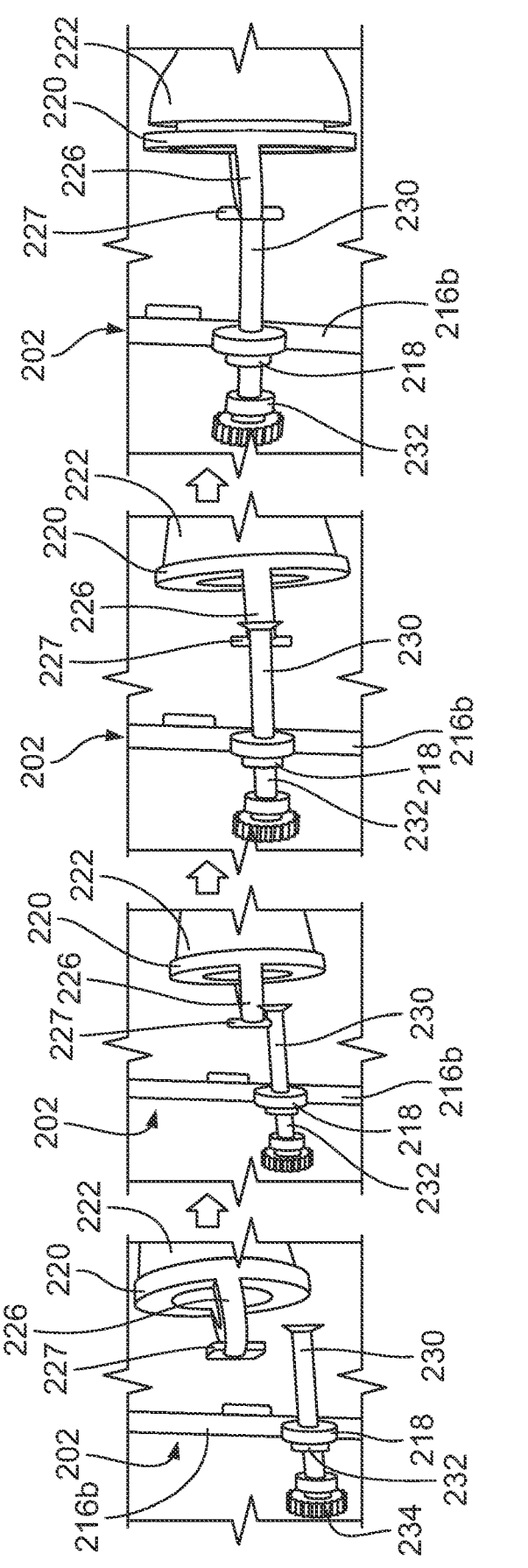
FIG. 2 illustrates an exemplary sequence of steps of attaching a tissue fitting structure with a vein to a bottom bar of a frame using an adjustable screw, in accordance with some embodiments of the present specification.

FIG. 2 illustrates an exemplary sequence of steps of attaching a tissue fitting structure 220 with a vein 222 to a bottom bar 216b of a frame 202 using an adjustable screw 230, in accordance with some embodiments of the present specification. The adjustable screw 230 is slipped through the connecting structure 227, which is a ring or protrusion, of a loop 226 attached to a first ring of the tissue fitting structure 220. The adjustable screw 230 is further threaded through a hole 218 on the bottom bar 216b to attach the corresponding end of vein 222 to the bottom side of the frame 202. In embodiments, the adjustable screw 230 is a flat head screw. The screw 230 is rotated through the threaded hole 218 on the bottom bar 216b. By virtue of the rotation or threading of the screw 230, the tissue fitting structure 220 moves downward toward the bottom bar 216b (or, correspondingly, upward toward the top bar 116a) until the desired length is achieved. In some embodiments, a bolt 232 with a diameter corresponding to the thickness of the adjustable screw 230 receives the screw 230 emerging through the hole 218. An adjustable thumb screw 234, attached to the adjustable screw 230 may then be adjusted to move the screw 230 until the vein 222 is elongated to a desired length or to a desired degree of tension. At all times, the tissue fittings (top and bottom) are oriented perpendicular to the top and bottom bars of frame 202, for optimal fluid flow. The tension practically is a result of changing the distance at which the vein is fixed. In embodiments, moving the fitting structure upward, by rotating the screw at the bottom tissue fitting in a first direction, causes the tension in the vein or conduit to decrease. Correspondingly, moving the fitting downward, by rotating the screw at the bottom tissue fitting in a second direction, opposite the first direction, causes the tension in the vein or conduit to increase. The end tension is maintained to be enough to have the vein or conduit standing in its full length and maintain a horizontal state when the frame is turned horizontally, but not too much to decrease the diameter, or change the shape, of the vein or conduit.

In alternate embodiments, other tension inducing mechanisms to elongate the tissue are used. In one embodiment, springs are used in place of screws 128 and 130. In one embodiment, springs are used in place of adjustable screws 130, while the top side of the tissue is fixed to frame 102 with screws 128. In one embodiment, hooks are used in place of either or both screws 128 and 130. One of ordinary skill in the art would appreciate that the tension inducing mechanism generally comprises a first holder, configured to atraumatically grasp an entire periphery of one open end of the vein or conduit, a second holder, configured to atraumatically grasp an entire periphery of the opposing open end of the vein or conduit, a first member configured to attach the first holder to the frame, and a second member configured to attach the second holder to the frame, wherein at least one of the first member or second member is configured to reduce or expand in a dimension, such as length, so as to apply a pulling force or tension to the vein or conduit.

Preferably, the tension inducing mechanism applies a vertical extending force to each end of the vein to increase the tension at the ends of the veins by at least 1% and no greater than 20%, and preferably at least 2% and no greater than 15%. The vein may be extended to a desired length such that the length of the vein, after applying the tension inducing mechanisms described herein, is in a range of 2 to 15 percent greater than its original, pre-extended length. The initial, unextended length and final extended lengths of the vein 122 may be observed and determined with the aid of scales-scale 114a and tapered scale 114.

Figure 4C:
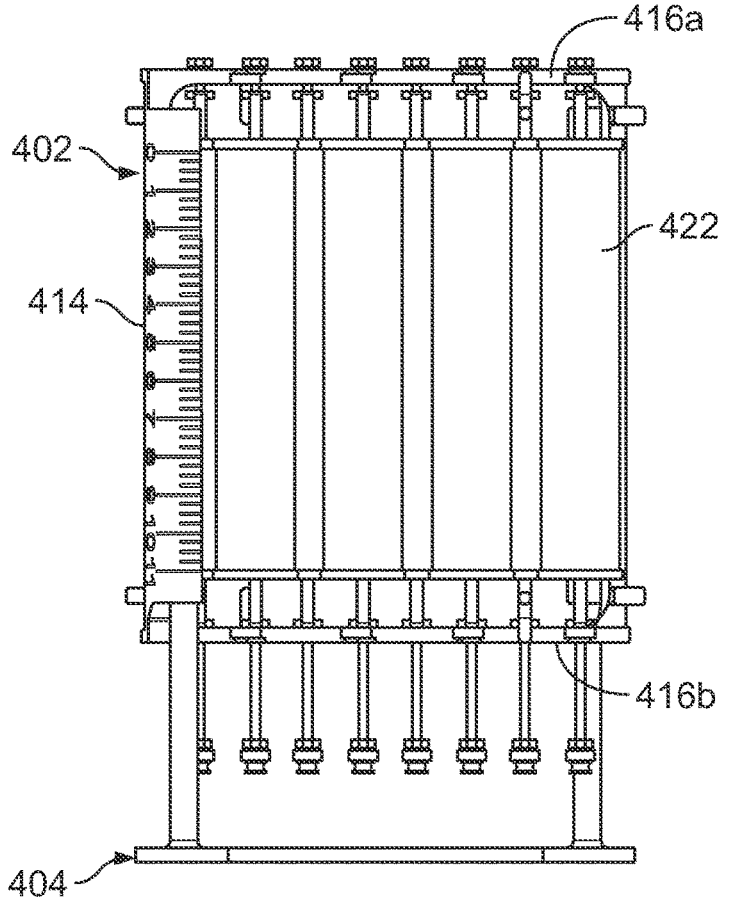
FIG. 4C illustrates multiple tissues mounted on a frame while the frame stands vertically on a stand, in accordance with some embodiments of the present specification.
Figure 4D:
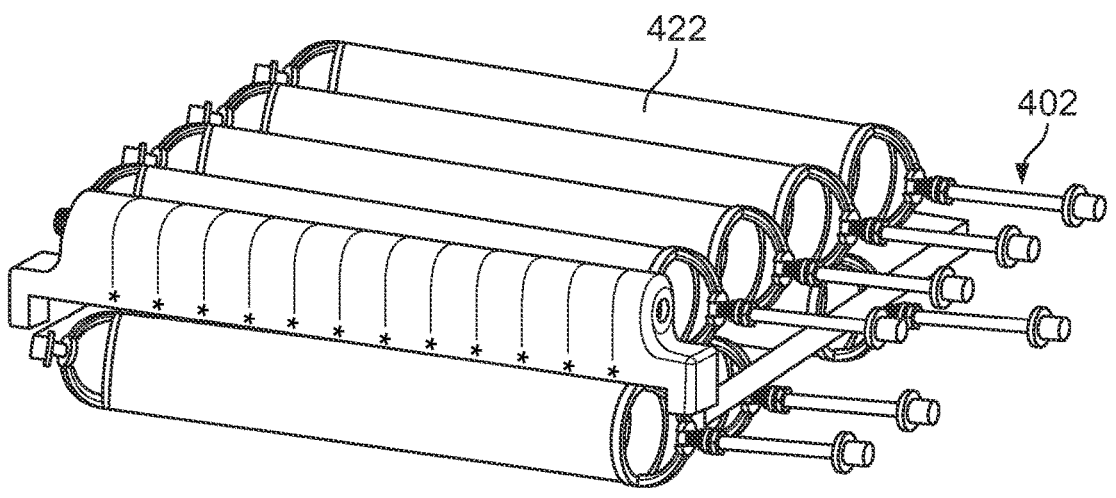
FIG. 4D illustrates the frame with the secured veins, after the frame is removed from its stand, in accordance with some embodiments of the present specification.

Referring again to FIG. 1, the vein 122 is elongated to have an open, and not a collapsed, internal lumen, and preferably without a deformation (such as a decrease of diameter) along the vein. Therefore, in one embodiment, the vein 122 is elongated until it has a substantially constant diameter across its length, where the term substantially constant shall mean that the diameter does not vary by more than 30% across its entire length, preferably does not vary by more than 25%, 20%, 15%, 10%, 5%, 1% or any numerical increment between 30% and 1%. The elongated, open-tube structure of the vein allows for the uniform and free flow of solutions during a subsequent decellularization process in a vessel. In embodiments, multiple tissues are attached to the frame 102 in a manner similar to attachment of vein 122. In some embodiments, frame 102 supports attaching up to four tissues. In some embodiments, frame 102 support attaching up to eight tissues, as shown in FIG. 4D. Once loaded with tissues such as vein 122, the frame 102 may be removed from the stand 104 by withdrawing elongated tubes 110 that extend from the frame 102 from the hollow extensions 108 so as to remove the frame 102 from the stand 104.

Figure 3:
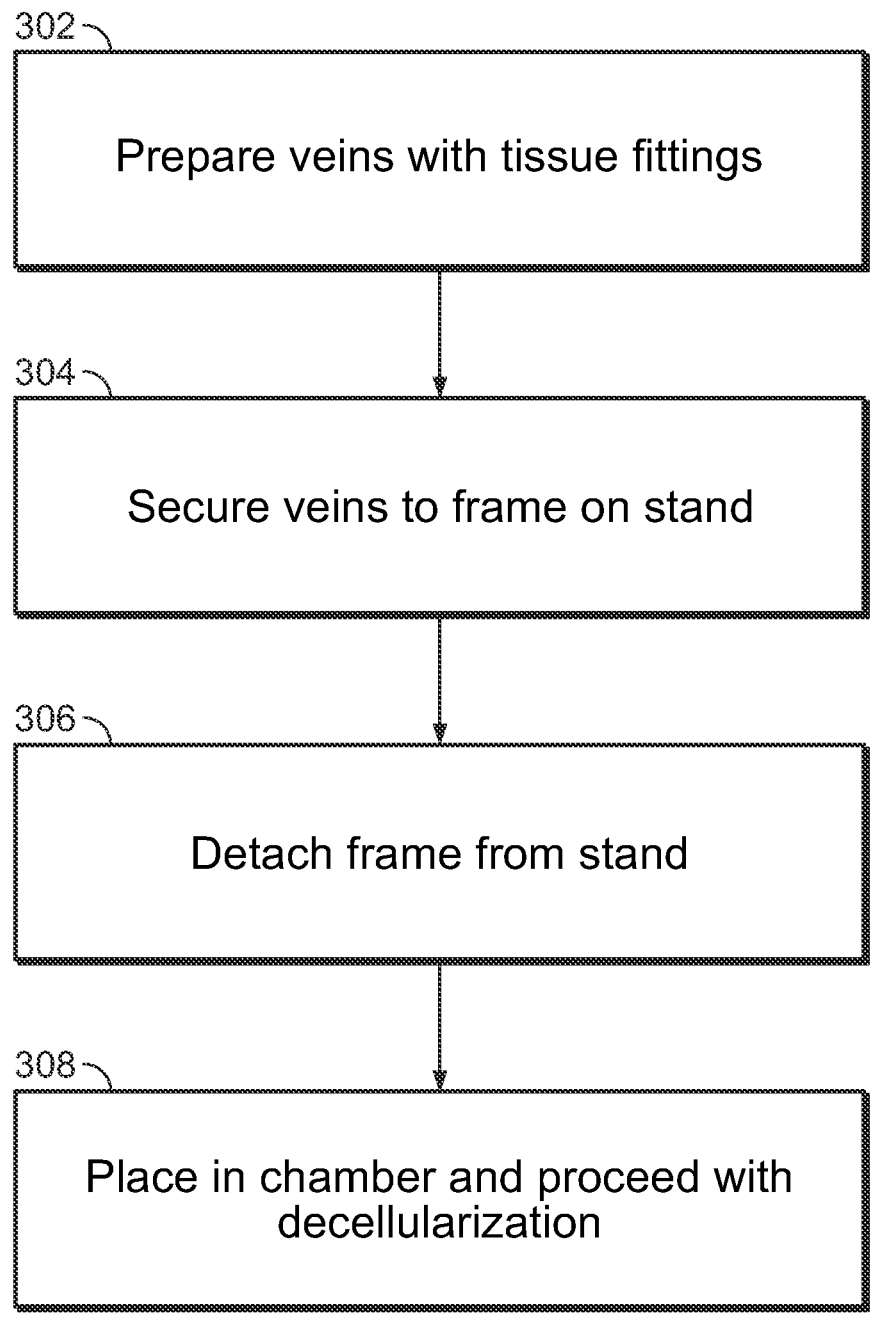
FIG. 3 is a flow chart illustrating exemplary steps of using the structure of FIG. 1 in accordance with some embodiments of the present specification.

FIG. 3 is a flow chart illustrating exemplary steps of using the structure 100 of FIG. 1, in accordance with some embodiments of the present specification. Referring simultaneously to FIGS. 1, 3, and 4A at step 302, tissues such as vein or conduit 122 are prepared with tissue fitting structures 120. Accordingly, tissue fitting structures 120 are attached to a top side and a bottom side of the vein 122. FIG. 4A illustrates a vein or conduit 422 attached to a tissue fitting structure 420 with a first ring 424. In some embodiments, a zip-tie is used to attach the opening of a tubular vein to a first ring portion 424 of the tissue fitting structure 420. At step 304, the vein 422, attached on its two open ends to a tissue fitting structure 420 each, is secured to the frame 402. Referring to FIGS. 4A and 4C simultaneously, one end of the vein or conduit 422 is attached to the top bar 416a and the other end is stretched and attached to the bottom bar 416b. The two tension inducing mechanisms, such as the screws, are manipulated to extend the vein 422 to a desired length, which is preferably 2 to 15 percent greater than the original length. FIG. 4C illustrates multiple tissues 422 mounted on a frame 402 while the frame stands vertically on a stand 404. The veins 422 are attached through tissue fitting structures 424 to a top bar 416a and a bottom bar 416b of the frame 402. Scales 414 are used to observe and determine the tension applied to the veins 422 while attaching them to the bottom bar 416b. At step 306, the frame 102, along with the secured veins 122, is removed from the stand 104. The veins 122 remain secured to the frame 102 with the aid of the tissue fitting structures 120. FIG. 4D illustrates the frame 402 with the secured veins 422, after the frame 402 is removed from its stand 404. At step 308, the frame 102 is placed within a chamber where the process if decellularization may be implemented.

Figures 5A, 5B, 5C:
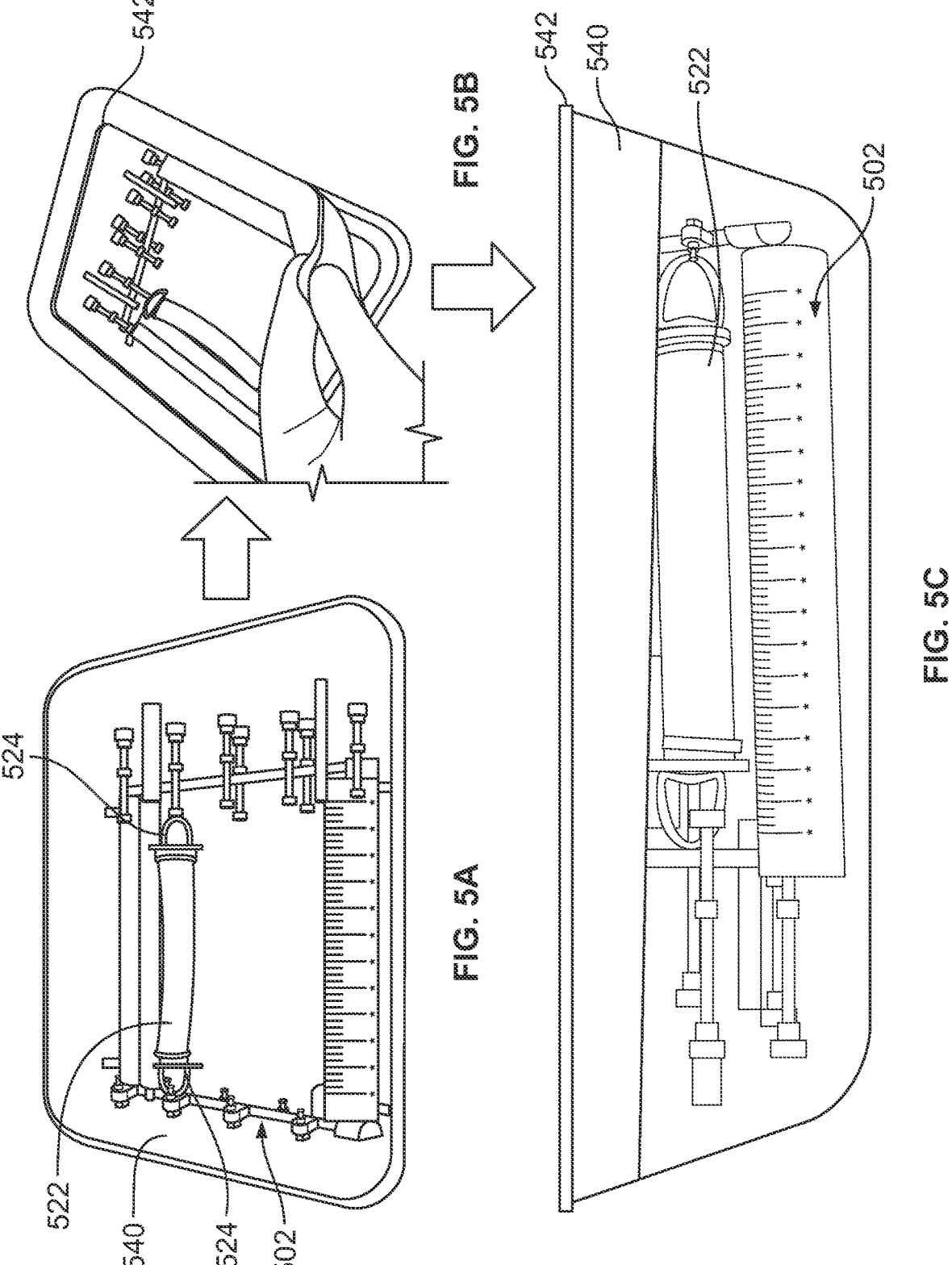
FIG. 5A is an illustration of a vein secured to a frame that is placed in a chamber.
FIG. 5B is an illustration of how the chamber of FIG. 5A is sealed with a cover.
FIG. 5C is an illustration showing a side-elevated view of the chamber of FIG. 5B filled with fluids for decellularization and sealed with the cover.

Removal from the frame is achieved by unhooking the fitting rings from the screws on the top and bottom horizontal bars and then the vein conduits are cut off the fixture below the zip tie attached to the tissue fitting structure. Decellularization Process FIGS. 5A, 5B, and 5C illustrate photographs of an exemplary sequence of steps for placing the veins 122 secured to the frame 102 in a chamber for decellularization. FIG. 5A is a photograph of a vein 522 secured to a frame 502 that is placed in a chamber 540. The frame 502 is placed horizontally for positioning within the chamber 540. The vein 522 remains firmly in its strained tubular form, supported by its attachment through tissue fitting structures 524 to the two sides of the frame 502. FIG. 5B is an illustration of how the chamber 540 is sealed with a cover 542. Referring to FIGS. 5A, 5B, and 5C simultaneously, the cover 542 includes a silicone boundary that is configured to securely form-fit the edges of chamber 540. FIG. 5C is an illustration depicting a side-elevated view of the chamber 540 filled with fluids for decellularization and sealed with the cover 542, during the decellularization process. In embodiments, approximately 1 to 250 milliliters (mL), and preferably 200 mL of the fluid is used for each vein conduit 522 in the frame 502. In some cases, 22 ml of fluid is used per square centimeter ($cm^2$) of surface of tissue.

In an eight-conduit configuration, the chamber 540 may hold approximately 1.8 liters of fluids. In some embodiments, in eight conduit configurations (eight vein conduits), the chamber 540 may hold a volume of fluid ranging from 1000 mL to 1250 mL. In some embodiments, in an eight-conduit configuration, the chamber 540 may hold a volume of the fluid ranging from 125 mL to 150 mL per vein conduit. It should be appreciated, that if the chamber 540 is used in a four-conduit configuration (four vein conduits) then the volume of the fluid used may not necessarily be half of the volume of the fluid used as with the case of using eight vein conduits since the vein conduits need to be completely immersed in the fluid. In some embodiments, in a four-conduit configuration, the chamber 540 may hold approximately 200 mL of fluid per vein conduit.

In an exemplary decellularization process, the tissues may be exposed to a plurality of fluids and a residence time as follows: one hour of 0.05M NaOH followed by six days of decellularization solution comprising 50 mM TRIS; 0.1 to 0.5% and preferably 0.25% sodium dodecyl sulfate (SDS); 0.1% to 1% and preferably 0.5% sodium deoxycholate (DOC); 0.1% to 1% and preferably 0.5% Triton X100; 0.1% to 1% and preferably 0.2% EDTA, followed by, on two consecutive days, two hours in a 70% Ethanol solution, followed by PBS wash, followed by four days DNAse/RNAse treatment, followed by a second PBS wash, followed by exposure to a solution of 0.1% peracetic acid, and followed by a wash and final PGG treatment.

In embodiments, the plurality of fluids for the decellularization process are sequentially changed, manually or automatically, in the chamber 540 regardless of the number of vein conduits (which may, in embodiments, range from 1 vein conduit to 12 vein conduits, and preferably from 1 vein conduit to 8 vein conduits) inside the chamber 540. In some embodiments, during a decellularization process, a first fluid of the plurality of fluids (that is sequentially changed) having a volume in the range of 1000 mL to 1500 mL is drained from the chamber 540 to be replaced with a second fluid of the plurality of fluids having a volume in the range of 1000 mL to 1500 mL, the second fluid of the plurality of fluids having a volume in the range of 1000 mL to 1500 mL is drained from the chamber 540 to be replaced with a third fluid of the plurality of fluids having a volume in the range of 1000 mL to 1500 mL, and so forth until the maximum number of fluid exchanges is reached. Also, in various embodiments, the residence time may range from an hour to one or more days depending upon the fluid, that a vein conduit is exposed to, during a decellularization process. In embodiments, the values above are scaled according to the total actual volume used in the process. As a non-limiting illustration, the tissues are one or more bovine jugular vein conduits.

In accordance with aspects of the present specification, the decellularization process, which may be achieved using decantation, aspiration, or removal of a first fluid from the chamber as well as refilling the chamber with a second replacement or fresh fluid is performed automatically and/or manually.

The above examples are merely illustrative of the many applications of the system of present specification. Although only a few embodiments of the present specification have been described herein, it should be understood that the present specification might be embodied in many other specific forms without departing from the spirit or scope of the invention. Therefore, the present examples and embodiments are to be considered as illustrative and not restrictive, and the specification may be modified within the scope of the appended claims.

We claim:

1. A processing system adapted to decellularize one or more pieces of biological tissue having a cylindrical shape, comprising:
   a processing device comprising:
      a frame configured to hold the one or more pieces of biological tissue, wherein each of the one or more pieces of biological tissue comprises a first end defined by a first circular periphery, a second end, opposing the first end, defined by a second circular periphery, and a length defined by a longitudinal axis that extends between the first end and the second end;
      a first holder comprising a first ring configured to atraumatically attach to the first circular periphery of at least one of the one or more pieces of biological tissue;
      a second holder comprising a second ring configured to atraumatically attach to the second circular periphery of at least one of the one or more pieces of biological tissue;
      a first member configured to attach the first holder to the frame; and
      a second member configured to attach the second holder to the frame, wherein at least one of the first member or second member is configured to lengthen or contract so as to apply tension along the longitudinal axis of the at least one of the one or more pieces of biological tissue to preserve its cylindrical shape;
   a chamber, wherein the processing device is configured to fit within an internal volume of the chamber; and
   a decellularization solution positioned within the internal volume of the chamber.

2. The processing system of claim 1, wherein the one or more pieces of biological tissue comprises a vein.

3. The processing system of claim 2, wherein the frame is configured to hold 4 to 10 pieces of said biological tissue.

4. The processing system of claim 1, wherein the first holder is configured to atraumatically attach to an entirety of the first circular periphery.

5. The processing system of claim 4, wherein the second holder is configured to atraumatically attach to an entirety of the second circular periphery.

6. The processing system of claim 1, further comprising a first measurement member attached to a first side of the frame, wherein the first measurement member comprises a plurality of measurement units.

7. The processing system of claim 6, wherein the first measurement member is vertically positioned and is configured as a cylinder with a tapering diameter across at least part of its length.

8. The processing system of claim 7, further comprising a second measurement member attached to an opposing second side of the frame, wherein the second measurement member comprises a plurality of measurement units.

9. The processing system of claim 8, wherein the second measurement member is vertically positioned and is configured as a cylinder with a tapering diameter across at least part of its length.

10. The processing system of claim 7, further comprising a stand adapted to support the frame during mounting of a tissue, wherein the stand comprises a base surface configured to be horizontally positioned on a flat surface and a pair of vertically protruding hollow extensions perpendicularly and fixedly attached to the base surface and wherein each extension is configured to attach to one end of the first measurement member.

11. The processing system of claim 1, wherein the frame comprises a top member extending along a top side of the frame and a bottom member extending along a bottom side of the frame.

12. The processing system of claim 11, wherein the top member comprises at least one first threaded hole, wherein the bottom member comprises at least one second threaded hole and wherein the at least one second threaded hole is vertically aligned with the at least one first threaded hole.

13. The processing system of claim 12, wherein the first holder further comprises a first semi-circular loop fixedly attached to the first ring, and wherein the first semi-circular loop comprises a first protrusion at a center of the first semi-circular loop.

14. The processing system of claim 13, wherein the second holder further comprises a second semi-circular loop fixedly attached to the second ring, and wherein the second semi-circular loop comprises a second protrusion at a center of the second semi-circular loop.

15. The processing system of claim 14, wherein the first member is at least one first threaded screw, wherein the at least one first threaded screw is configured to pass through the first protrusion and the at least one first threaded hole and wherein the at least one first threaded screw is further configured to apply said tension upon being turned.

16. The processing system of claim 15, wherein the second member is at least one second threaded screw, wherein the at least one second threaded screw is configured to pass through the second protrusion and the at least one second threaded hole and wherein the at least one second threaded screw is further configured to apply said tension upon being turned.

17. The processing system of claim 14, wherein the first ring has a first diameter and the first protrusion has a second diameter and wherein the first diameter is larger than the second diameter.

18. The processing system of claim 1, further comprising a zip tie, wherein the zip tie is adapted to secure at least one of the first holder to the first circular periphery or the second holder to the second circular periphery.

19. The processing system of claim 1 wherein the at least one of the first member or second member is configured to apply the tension to elongate the at least one of the one or more pieces of biological tissue in a range of 2 to 10 percent.

20. The processing system of claim 1, further comprising:
a third holder configured to atraumatically attach to a periphery of one open end of at least a second one of the one or more pieces of biological tissue;

a fourth holder configured to atraumatically attach to a periphery of an opposing open end of the at least second one of the one or more pieces of biological tissue;
a third member configured to attach the third holder to the frame; and
a fourth member configured to attach the fourth holder to the frame, wherein at least one of the third member or fourth member is configured to lengthen or contract so as to apply tension to the at least second one of the one or more pieces of biological tissue.

21. The processing system of claim 20, further comprising:
a fifth holder configured to atraumatically attach to a periphery of one open end of at least a third one of the one or more pieces of biological tissue;
a sixth holder configured to atraumatically attach to a periphery of an opposing open end of the at least third one of the one or more pieces of biological tissue;
a fifth member configured to attach the fifth holder to the frame; and
a sixth member configured to attach the sixth holder to the frame, wherein at least one of the fifth member or sixth member is configured to lengthen or contract so as to apply tension to the at least third one of the one or more pieces of biological tissue.

22. The processing system of claim 21, further comprising:
a seventh holder configured to atraumatically attach to a periphery of one open end of at least a fourth one of the one or more pieces of biological tissue;
an eighth holder configured to atraumatically attach to a periphery of an opposing open end of the at least fourth one of the one or more pieces of biological tissue;
a seventh member configured to attach the seventh holder to the frame; and
an eighth member configured to attach the eighth holder to the frame, wherein at least one of the seventh member or eighth member is configured to lengthen or contract so as to apply tension to the at least fourth one of the one or more pieces of biological tissue.

23. The processing system of claim 22, further comprising:
a ninth holder configured to atraumatically attach to a periphery of one open end of at least a fifth one of the one or more pieces of biological tissue;
a tenth holder configured to atraumatically attach to a periphery of an opposing open end of the at least fifth one of the one or more pieces of biological tissue;
a ninth member configured to attach the ninth holder to the frame; and
a tenth member configured to attach the tenth holder to the frame, wherein at least one of the ninth member or tenth member is configured to lengthen or contract so as to apply tension to the at least fifth one of the one or more pieces of biological tissue.

24. The processing system of claim 23, further comprising:
an eleventh holder configured to atraumatically attach to a periphery of one open end of at least a sixth one of the one or more pieces of biological tissue;
a twelfth holder configured to atraumatically attach to a periphery of an opposing open end of the at least sixth one of the one or more pieces of biological tissue;
an eleventh member configured to attach the eleventh holder to the frame; and a twelfth member configured to attach the twelfth holder to the frame, wherein at least one of the eleventh member or twelfth member is configured to lengthen or contract so as to apply tension to the at least sixth one of the one or more pieces of biological tissue.

25. The processing system of claim 22, wherein each of the first holder and second holder, third holder and fourth holder, fifth holder and sixth holder, and seventh holder and eighth holder are vertically aligned with each other.

* * * * *